US00PP11607P

United States Patent [19]

Boeder

[11] Patent Number: Plant 11,607

[45] Date of Patent: Oct. 31, 2000

[54] CHRYSANTHEMUM PLANT NAME 'KOOKABURRA'

[75] Inventor: Mark Boeder, West Wittering, United Kingdom

[73] Assignee: Cleangro Limited, United Kingdom

[21] Appl. No.: 09/189,714

[22] Filed: Nov. 11, 1998

[51] Int. Cl.[7] ..... A01H 5/00

[52] U.S. Cl. ..... Plt./290

[58] Field of Search ..... Plt./290, 296

[56] References Cited

U.S. PATENT DOCUMENTS

P.P. 3,896 6/1976 Jessel, Jr. et al. ..... Plt./290

*Primary Examiner*—Howard J. Locker

*Attorney, Agent, or Firm*—Christie, Parker & Hale, LLP

[57] ABSTRACT

A new plant variety of chrysanthemum producing orange bronze flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Kookaburra'.

The female parent of the new variety is an undistributed seedling identified as 'G33 C12' and the male parent is an undistributed seedling identified as 'G19 C2'. The new variety has been asexually reproduced by vegetative cuttings in Ventura County, Calif. and the distinguishing characteristics are retained through successive generations of asexual reproduction.

SUMMARY OF THE INVENTION

'Kookaburra' is a chrysanthemum plant variety with orange bronze flowers.

BRIEF DESCRIPTION OF ILLUSTRATION

The accompanying photograph shows typical specimens of the plant and flowers of the new variety with colors being as nearly true as possible with illustrations of this type.

DESCRIPTION OF THE PLANT

The following description of the new variety is of specimens grown in a greenhouse in Ventura County, Calif. in the month of April. 'Kookaburra' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Kookaburra' is about 26 days and a response time of about 6.5 weeks. No treatment with growth retardant was used with plants described. Useful growing conditions include night temperatures of about 18°–20° C., day temperatures of about 20°–30° and about 5,000 to 6,000 foot-candles of light. Then new variety is naturally blooming in the middle of September in Ventura County, Calif.

Plant:

*Habit*.—Mounding, herbaceous perennial, full branching.

*Height*.—About 32 cm.

*Number of breaks from pinch*.—About 3 to 4.

*Length of lateral branches*.—About 27 cm.

*Stem color*.—Near 137D.

*Leaf arrangement*.—Alternate.

*Number of leaves per lateral branch*.—About 14 fully expanded leaves.

*Leaf size*.—Length: About 5.3 cm. Surface: Lightly pubescent.

*Flower bud* (*when just showing color*).—Color: Near 16C. Diameter: About 0.9 cm. Height: About 0.6 cm.

*Ray florets*.—Number per inflorescence: About 110. Texture: Matte. Shape: Oblong. Apex: 2 to 3 irregular obtuse lobes. Base: Truncate. Margin: Entire. Aspect: Undulating. Length: About 2.5 cm. Width: About 0.5 cm.

*Disc florets*.—Number per inflorescence: About 10. Texture: Shiny. Shape: Cylindrical. Length: About 0.4 cm. Width of disc: About 0.8 cm.

*Fragrance*.—Faint.

*General inflorescence coloration*.—Orange/bronze.

*Type of inflorescence*.—Decorative.

*Ray florets, top side*.—Immature: Near 169A. Mature: Near 26A. Fading: Near 26B.

*Ray florets, under side*.—Immature: Near 26A. Mature: Near 26B. Fading: Near 20A.

*Disc florets*.—Immature: Near 154B.

*Leaf shape*.—Ovate. Attachment: Petioled. Leaf apex: Obtuse. Base: Tapered, truncate. Margin: Palmately lobed. Aspect: Slightly undulating. Surface: Top: Lightly pubescent. Bottom: Lightly pubescent.

*Venation color*.—Underside: Near 137D. Upper side: Near 146C.

*Petiole*.—Length: About 1.3 cm. Color: Near 146C.

*Mature leaf color*.—Top: Near 137A. Bottom: Near 137C.

*Young leaf color*.—Top: Near 137A. Bottom: Near 137D.

Inflorescence:

*Form*.—Cyme.

*Flower form*.—Decorative.

*Number of blooms per branch*.—About 11.

*Diameter of fully expanded bloom*.—About 5 cm.

*Depth of fully expanded bloom*.—About 1.8 cm.

*Sepal number*.—About 20. Color: Near 137B. Length: About 0.7 cm. Width: About 0.3 cm.

*Peduncle*.—Terminal: About 5 cm in length. Lateral: About 9 cm in length. Habit: Straight.

*Changes as the flower ages*.—Color fades to orange/gold.

Reproductive organs:

*Ray florets*.—Pistillate. Stigma shape: 2 forked. Stigma color: Near 12A. Style length: About 0.5 cm. Style color: Near 154C.

*Disc florets*.—Stigma shape: Linear. Stigma color: Near 7B. Style length: About 0.4 cm. Style color: Near 2D. Stamen number: About 5. Anther length: About 0.3 cm. Pollen color: Near 16A. Pollen quantity: Minimal.

What is claimed is:

1. A new and distinct chrysanthemum plant of the variety substantially as herein shown and described.

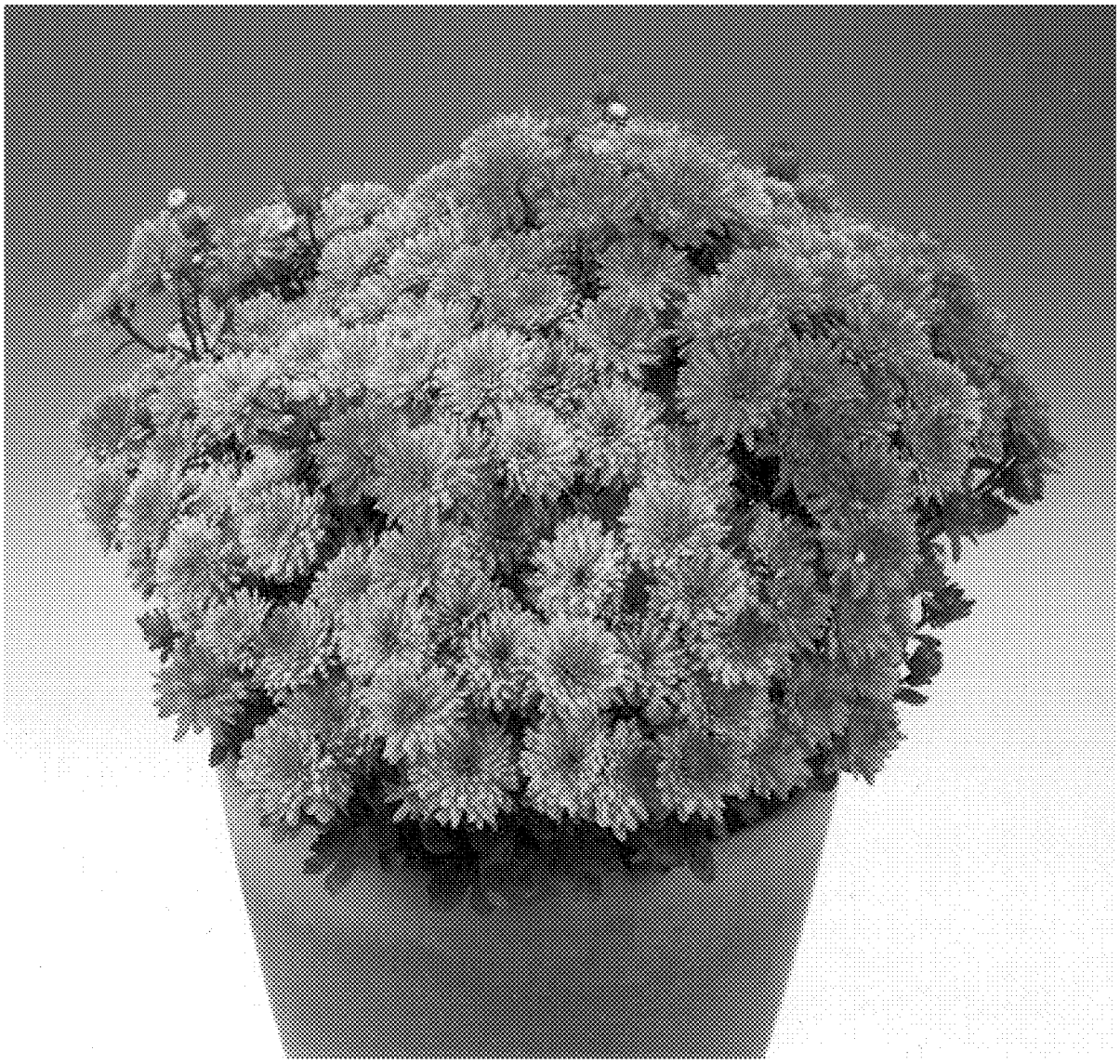

* * * * *